United States Patent [19]
Johnson

[11] Patent Number: 5,939,634
[45] Date of Patent: Aug. 17, 1999

[54] LIQUID MEASURING SYSTEM AND METHODS

[75] Inventor: Glen A. Johnson, Mesa, Ariz.

[73] Assignee: Arizona Instrument Corporation, Phoenix, Ariz.

[21] Appl. No.: 09/031,489

[22] Filed: Feb. 26, 1998

Related U.S. Application Data

[62] Division of application No. 08/401,874, Mar. 10, 1995, Pat. No. 5,765,433.

[51] Int. Cl.$^6$ .................................................. G01N 9/04
[52] U.S. Cl. ................................ 73/596; 73/602; 73/627
[58] Field of Search .................................. 73/579, 290 V, 73/290 R, 291, 596, 602, 627; 340/621; 367/108, 908; 702/36, 39, 54, 55

[56] References Cited

U.S. PATENT DOCUMENTS

| | | | |
|---|---|---|---|
| 4,803,638 | 2/1989 | Nottingham et al. | 702/36 |
| 5,031,467 | 7/1991 | Rambow | 73/861.25 |

Primary Examiner—Hezron Williams
Assistant Examiner—Thuy Vinh Tran
Attorney, Agent, or Firm—Meschkow & Gresham, P.L.C; Jordan M. Meschkow; Lowell W. Gresham

[57] ABSTRACT

Ultrasonic apparatus determines the fluid depth, volume, and temperature in a storage tank. A system description for monitoring an underground storage tank containing gasoline is described. The system determines the water's and gasoline's depth, volume, and temperature. The apparatus consists of a remote console, ultrasonic probe, and interconnecting cable. The remote console contains a display to report tank information and a computer to operate the probe. The probe consists of an ultrasonic transducer above the bottom of the probe facing upwards to transmit and receive ultrasonic signals, vertically spaced reflectors and a temperature sensor to measure fluid temperature.

1 Claim, 5 Drawing Sheets

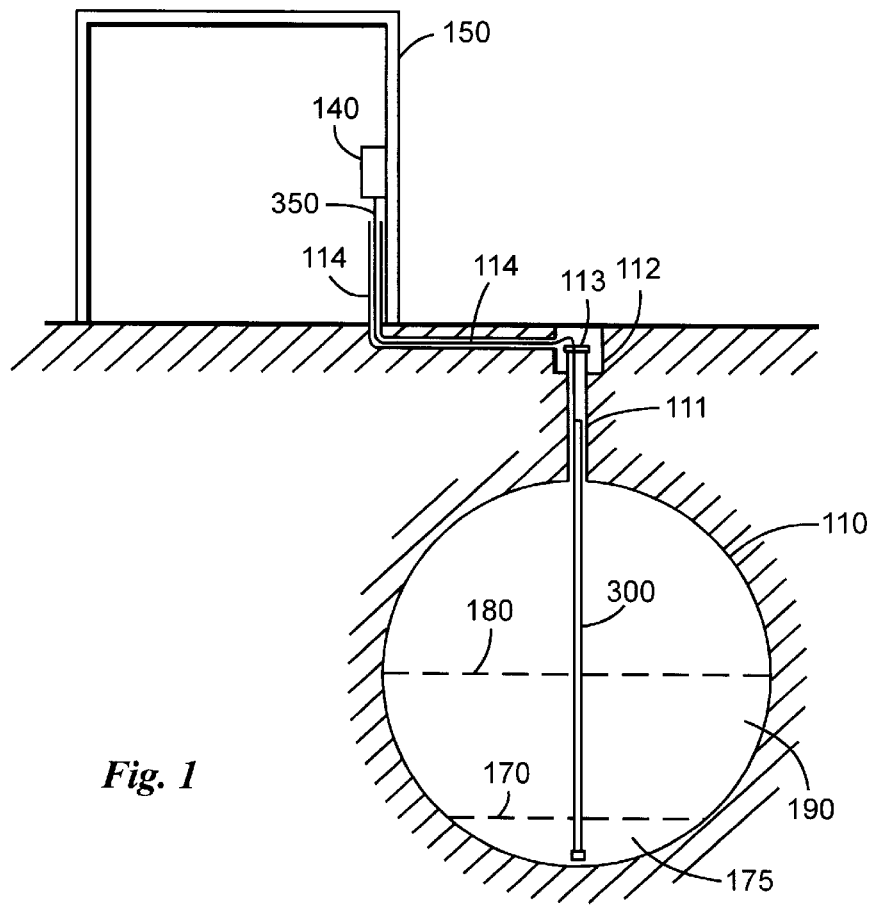
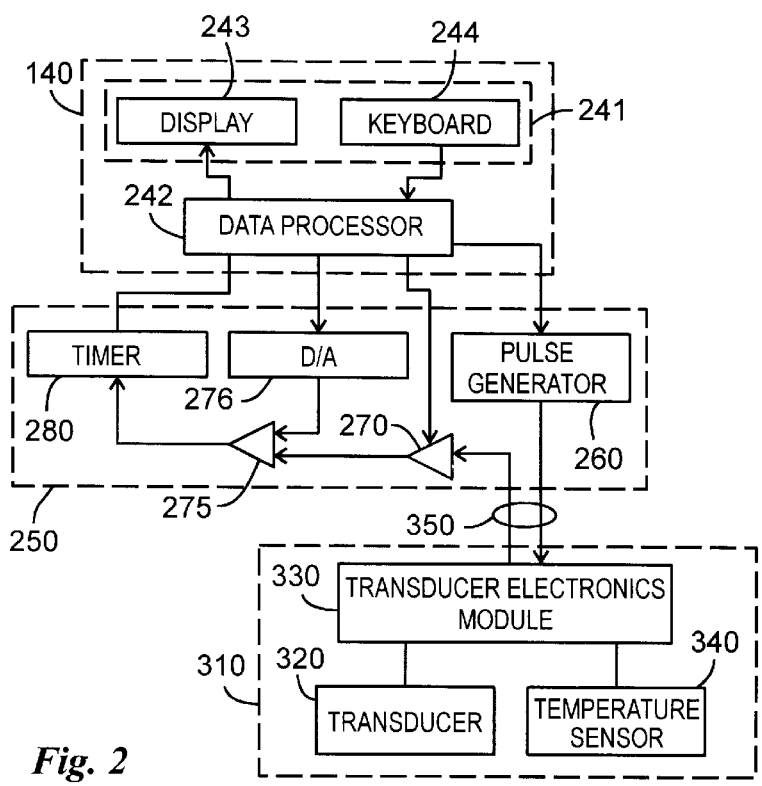
Fig. 1
Fig. 2

LIQUID MEASURING SYSTEM AND METHODS

This is a divisional of an application under 35 CFR 1.60, of pending prior application Ser. No. 08/401,874, filed on Mar. 10, 1995 for LIQUID MEASURING SYSTEM AND METHODS, now U.S. Pat. No. 5,765,433.

BACKGROUND OF THE INVENTION

This invention relates generally to the measuring of the volume of liquid in a tank using ultrasound, and, in particular, relates to the measuring of the volume of liquid in underground fuel storage tanks.

Many liquids are stored in tanks where the volume of the liquid in the tank cannot be directly observed. In many instances, the liquids are fuels such as gasoline and the tanks are large underground tanks. In the past a very common way of determining the volume in such a tank was to insert a calibrated rod and read the height of the liquid from the line formed on the rod by the liquid surface. This method, however, is not very precise and there are inherent errors in utilizing such an approach. One very serious drawback of the lack of precision is the inability to detect the loss of gasoline due to leakage. It is readily apparent that a leakage of gasoline or fuel from underground tanks can cause substantial environmental problems. It is desirable to detect such leaks before the problems become severe. Furthermore, state and federal regulations are beginning to mandate requirements for the detection of fuel leakage.

Currently, the EPA requires underground storage tanks to undergo leak tests. The EPA requires the tanks to be checked monthly with a system capable of detecting a 0.2 gallons per hour leak or yearly with a system capable of detecting a 0.1 gallons per hour leak. Systems presently on the market generally measure depth changes of less than 0.001 inches and temperature changes of less than 0.001° C.

The market is extremely price sensitive because tank owners desire to comply with regulations at minimal expense. Liquid measuring systems which utilize magnetostrictive and ultrasonic probes are the most popular in the market today. Magnetostrictive probes are higher priced giving ultrasonic probes a price advantage. Thus, it is desirable to provide an ultrasonic system.

Systems are now available which utilize ultrasonic transducers and ultrasound to determine the volume of liquid and typically place the transducer at the end of a probe and insert the probe into the fuel tank. The probe typically includes reflectors spaced along its length at precisely known distances from the transducer.

In one such known arrangement, the reflectors appear on the outside surface of the probe and are equally spaced apart. In operation, such a prior art system periodically transmits bursts of ultrasonic energy from the transducer. The burst of sonic energy produces echoes off of each of the submerged reflectors and off of the liquid/air surface interface. The echo received from the surface is typically the strongest echo because the large surface area reflects a greater amount of energy than would any of the reflectors positioned on the probe. The transmitted burst typically includes several ringing cycles. The echo signal waveforms likewise includes several ringing cycles. In the prior system, a receiver sensitivity is initially set at a minimum value and is successively increased until an echo signal is received. From that point, a series of echoes are analyzed in order to identify the first cycle in the echo signal waveform. Once the first cycle has been identified, it is used as a reference point to determine the echo delay times. The system then proceeds through an algorithm to identify every submerged reflector with the goal of identifying the topmost submerged reflector. When the topmost submerged reflector is identified, the echo delay time from the topmost reflector is utilized to calculate an average sonic velocity through the fuel. Based upon this average sonic velocity and the echo time received from the surface of the fuel, the depth of the liquid in the tank is calculated.

In addition, many approaches have been utilized to compensate for variations in the volume of the liquid with temperature. Again, in the prior above identified system, a temperature reading is taken at a point near the ultrasonic transducer. The sonic velocity between the transducer and the lowest reflector is measured to produce a reference sonic velocity at a reference temperature. The prior systems then proceed to determine an average temperature directly from the average sonic velocity in the liquid. The calculated volume of liquid in the tank is then adjusted to compensate for the temperature which is determined from the change in the average sonic velocity.

Still a further desirable aspect of any such measuring or gauging system is to accurately determine the depths of water in the fuel tank. In the prior system, the transducer is suspended in the tank such that it would be above the fuel/water interface. By relying upon multiple reflection of the ultrasonic energy from the transducer to the fuel/air interface back to the water/fuel interface and reflected back to the fuel/air interface and back to the transducer, the level of the water in the tank would be calculated.

The present invention is directed to providing an improved ultrasonic apparatus for measuring and remotely displaying the amount of liquid in a tank that provides for significantly improved accuracy in determining the volume and significantly improved accuracy in determining a temperature compensated volume and further, more accurately measuring the volume of water in a tank so that the volume of fuel can be more accurately calculated.

SUMMARY OF THE INVENTION

In accordance with the principles of this invention, an ultrasonic measuring system for measuring the amount of liquid in a tank has been developed. This system utilizes a probe which is inserted into a fuel tank and which carries at its lower end an ultrasonic transducer. The transducer is positioned to be at the bottom of the fuel tank and transmits ultrasonic energy upward into the liquid. The ultrasonic transducer receives echoes and from those echoes determines the height of liquid in the tank with a high degree of accuracy.

In accordance with the principles of this invention, the depth of the liquid in the tank is determined by measuring the echo delay time from the topmost submerged reflector to the transducer and the next topmost submerged reflector to the transducer. From these two measurements, the average sonic velocity in the strata of the tank immediately adjacent to the topmost strata is determined. The difference in the echo delay time between the signal received from the fuel/air surface and the topmost submerged reflector is combined with the average sonic velocity of the strata determined as set forth above to determine the height of the fuel above the topmost submerged reflector. To this distance is added the precisely known distance from the bottom of the tank to the topmost submerged reflector. With this arrangement, a very precise determination of the depth of the liquid in the tank is made.

Further in accordance with the invention, once the depth of liquid in the tank is precisely determined, the average sonic velocity in the tank may be calculated and the system operated in a mode in which measurements may be taken solely of the echo delay time between the liquid/air interface and the bottom of the tank and utilizing these measurements in combination with the calculated average sonic velocity, the depth of the liquid may be determined and from the depth, the volume.

Further in accordance with another aspect of the invention, the calculated volume of liquid in the tank is compensated according to temperature variations. The temperature compensation is, however, performed over strata in the tank. The strata are determined by pairs of reflectors. In accordance with the invention, the change in sonic velocity between pairs of reflectors is utilized to determine the change in temperature from an earlier measurement and the strata between the pair of reflectors. The change in temperature for a strata is then utilized to determine a temperature corrected volume for the strata. The summation of the temperature corrected volumes for the various strata in the tank provide for a temperature compensated volume.

Still further in accordance with the invention, a highly accurate method is used to precisely identify corresponding portions in the echo waveforms. In accordance with the invention, a profiling of the characteristics of the echo signals from the various reflectors and the fuel/air interface is conducted. During this profiling operation, the peak amplitudes of the reflected echo signals are measured and the largest range in magnitude between cycle peaks in the waveform received are determined. The objective is to identify that portion of the reflected waveform which has the largest magnitude of swing above the peak of other portions of the waveform.

Still further in accordance with the invention, it has been found that the positioning of reflectors within the probe is advantageous. In addition, it has been found to be advantageous to have the reflectors on the probe spaced apart not equidistant but at distances which are equivolumetric. For a tank of generally circular cross section, the distances between reflectors which are closer to the middle of the tank would therefore be closer than the distances between reflectors closer to the top and bottom of the tank.

BRIEF DESCRIPTION OF THE DRAWINGS

The invention will be better understood from a reading of the following detailed description of a preferred embodiment in which:

FIG. 1 illustrates the application of the present invention to a gasoline service station having an underground fuel tank positioned at a location remote from that of the service attendant;

FIG. 2 illustrates in block diagram form the system shown in FIG. 1;

DETAILED DESCRIPTION

Figure 3:
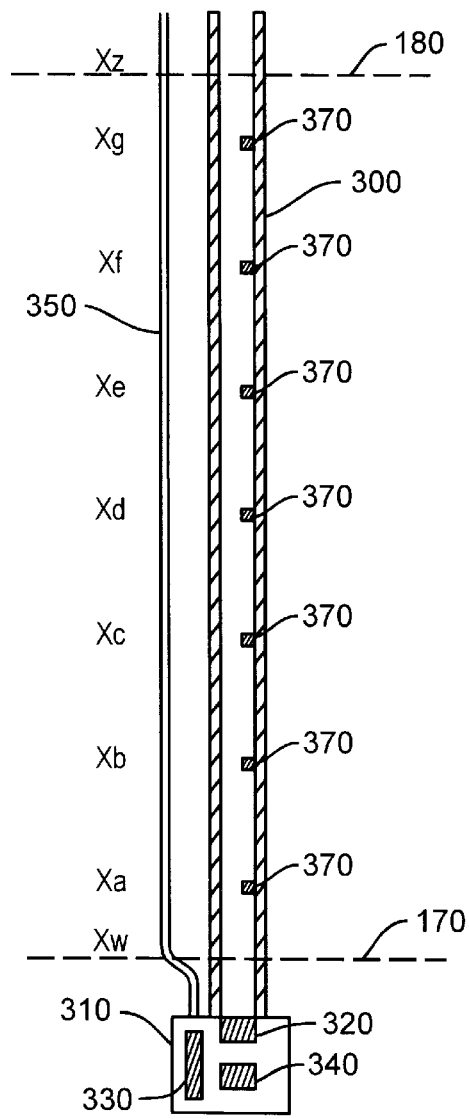
FIG. 3 illustrates a probe of the type utilized in the present invention.

Turning now to FIG. 1, a typical underground fuel tank installation at a gasoline service station is shown. The tank is only about one half full and the surface or fuel/air interface 180 of the fuel 190 is shown. Typically, fuel tanks will also contain water 175 from condensation. Because of the different densities, the water will be at the bottom of the tank. A fuel/water interface 170 occurs as a result. The underground fuel tank 110 has extending upwardly therefrom a riser 111 which terminates in a containment box 112. At the upward end of the riser 111, a riser cap 113 is provided. In a typical arrangement utilized at service stations, the riser 111 and riser cap 113 may form part of a Stage one vapor recovery system. In such systems, during the refueling of the underground tank, a vapor recovery hose is connected between the fuel truck and a vapor recovery vent on the fuel tank, in addition to the fuel hose which is connected between the fuel truck and the fill riser (which is not shown in the drawing) on the underground tank. While fuel is loaded into the tank via the fuel hose, the tank vapors are routed back to the fuel truck via the vapor recovery vent and the hose connection to the truck. Thus the riser cap 113 is removed during refueling to permit connection to the vapor recovery hose.

Supported in the riser is an ultrasonic probe or waveguide 300 which is shown in greater detail in FIG. 3. The probe or waveguide 300 is of tubular form and at its bottom end has affixed thereto a transducer module 310. The transducer module 310 includes an ultrasonic transducer 320, a temperature sensor 340 and a transducer electronics module 330. Both the transducer 320 and the temperature sensor 340 are connected to the transducer electronics module 330 which in turn is coupled to the console circuitry 250 via a three wire cable 350. The details of the transducer electronics module are disclosed in my copending U.S. patent application filed on even date herewith titled Transducer Module Circuitry and assigned to a common assignee. The subject matter of the patent application is specifically incorporated herein.

The probe or waveguide assembly 300 includes calibration reflectors 370 positioned within the probe along its inner surface. The reflectors 370 are spaced apart at distances which represent equal volumetric segments of the fuel tank. In contrast to the probe of this illustrative embodiment other probe assemblies are known in which the reflectors are spaced apart by equal distances along the length of the probe. It has been found advantageous to have the reflectors 370 which are further away from the transducer 320 to be of longer length to increase the size of the reflected signal. Each reflector 370 is flat on its bottom to create a maximum echo reflection.

The transducer module 310 is connected to a cable 350 which may be run through a conduit 114 as shown in FIG. 1. In some instances, the cable 350 is not run through the conduit 114 but rather is directly buried in the ground. The cable 350 terminates at a remote console 140. The remote console 140 is typically located in a building 150 which may be the service station building, or a remote building located on the premises.

Although only one underground storage tank 110 is shown in the drawing of FIG. 1, it should be readily apparent to those skilled in the art that gasoline stations typically have more than one underground fuel storage tank and the present invention is applicable to arrangements having a plurality of underground fuel storage tanks. In those arrangements an ultrasonic probe 300 in each tank is coupled to the console 140.

Turning now to FIG. 2, the remote console 140 includes a user interface 241 and a data processor 242. The user interface 241 includes a display 243 and may also include a keyboard 244 or a push button arrangement for selection of display information and for controlling the operation of the system. The data processor 242 can be a microprocessor or it can be a personal computer of the type well-known in the art. The remote console 140 is utilized to display tank information which is determined from the system. The data processor 242 is utilized to control the operation of the transducer electronics 250 and to analyze the data signals received from the transducer module 310 to operate the tank measurement system including performing calculations based on the data received. The data processor 242 can determine and display the volume of fuel in the tank as well as the volume of water in the tank. In addition, the system can provide for temperature compensated volume change measurements. Still further, the system can be utilized to inventory product as well as to detect leakage from the tank at very low loss rates.

Pulse generator 260 is controlled by the data processor 242 to cause the ultrasonic transducer 320 to generate ultrasonic signals in the tank. Because of the potentially explosive environment in the fuel tank, the manner in which the transducer 320 is pulsed must be intrinsicly safe. There are several ways to provide pulse signals to the transducer. However, one particularly advantageous arrangement is disclosed in my aforementioned copending patent application filed on even date herewith. When the transducer 320 is excited by the application of a pulse signal, it produces an output waveform which is a multicycle ringing waveform. When the ultrasonic waveform hits a reflector 370 or the fuel/air interface 180 or a fuel/water interface 170, an echo or reflection signal is generated. The ultrasonic transducer 320 not only responds to an electrical signal to produce an ultrasonic signal waveform, but also responds to the receipt of an ultrasonic waveform to produce a corresponding electrical signal output.

Each echo or reflected signal which is received by the transducer 320 is coupled via cable 350 to a programmable amplifier 270 which, in turn, is supplied to a comparator 275 which compares the output of the amplifier with a threshold signal that is determined by digital to analog convertor 276 which is, in turn, controlled by the data processor 242. A timer 280 is started each time an echo is received and stopped on receipt of a subsequent echo signal. The comparator 275 is utilized to determine the time sequence of signals detected by the transducer.

The system probe operation involves many steps. The data processor 242 specifies a pulse power and then commands the pulse generator 260 to transmit. The pulse generator 260 drives the ultrasonic transducer 320 with a burst of electrical energy that is proportional to the pulse level. The transducer 320 converts the electrical energy into ultrasonic energy. An ultrasonic burst travels upward through the tank. With reference to FIGS. 1 and 3, returning echoes are created by the fuel/water interface 170, fuel/air interface 180, and submerged calibration reflectors 370. The returning echoes travel downward through the fluid. When the returning echoes impact the transducer 320, the transducer 320 converts the ultrasonic energy back to electrical energy. The gain of amplifier 270 may be varied in steps from +5, +10, +30 and +40 and must be adjusted to allow comparator 275 to trigger on the returning echoes. The data processor 242 adjusts the comparator's 275 sensitivity by adjusting the pulse generator's 260 level, programmable amplifier's 270 gain, and/or the threshold voltage produced by digital to analog convertor 276. When the comparator 275 triggers on an echo, the timer 280 transmits the current time to the data processor 242. The data processor 242 records the echo times. The data processor 242 also reads the probe's temperature sensor 340. The water and gasoline depth, volume, and temperature are calculated from the measured information.

By positioning the transducer module 310 at the tank bottom, the fuel/water interface is detected when the interface rises above transducer 320. In addition, the height of the first reflector up from the bottom is chosen to be higher than any normal anticipated water level in the tank.

The water depth, designated as Xw, is calculated by using the measured fuel/water echo time designated as tw. Because water measurement accuracy is not critical, a constant speed of sound for water, designated as vw, is used. The depth of water is calculated with Xw=vw*tw/2.

The water volume, designated as Vw, is calculated from Xw and the tank manufacturer's tank chart. The tank chart converts depth amounts to volume amounts. The tank chart is stored by the data processor 242, and the data processor interpolates conversions that are between chart points.

The gasoline depth, designated by Xz, is calculated by using the measured air/gasoline echo time, designated as tz, and submerged calibration reflector echo times designated as ta, tb, tc, etc.

The gasoline volume, designated by Vz, is calculated from Xz in the same manner as the water volume.

The gasoline temperature, designated by Ttotal, is calculated by using the measured air/gasoline echo time, designated as tz, submerged calibration reflector echo times designated as ta, tb, tc, etc., and the measured temperature designated as Tt.

Figure 5:
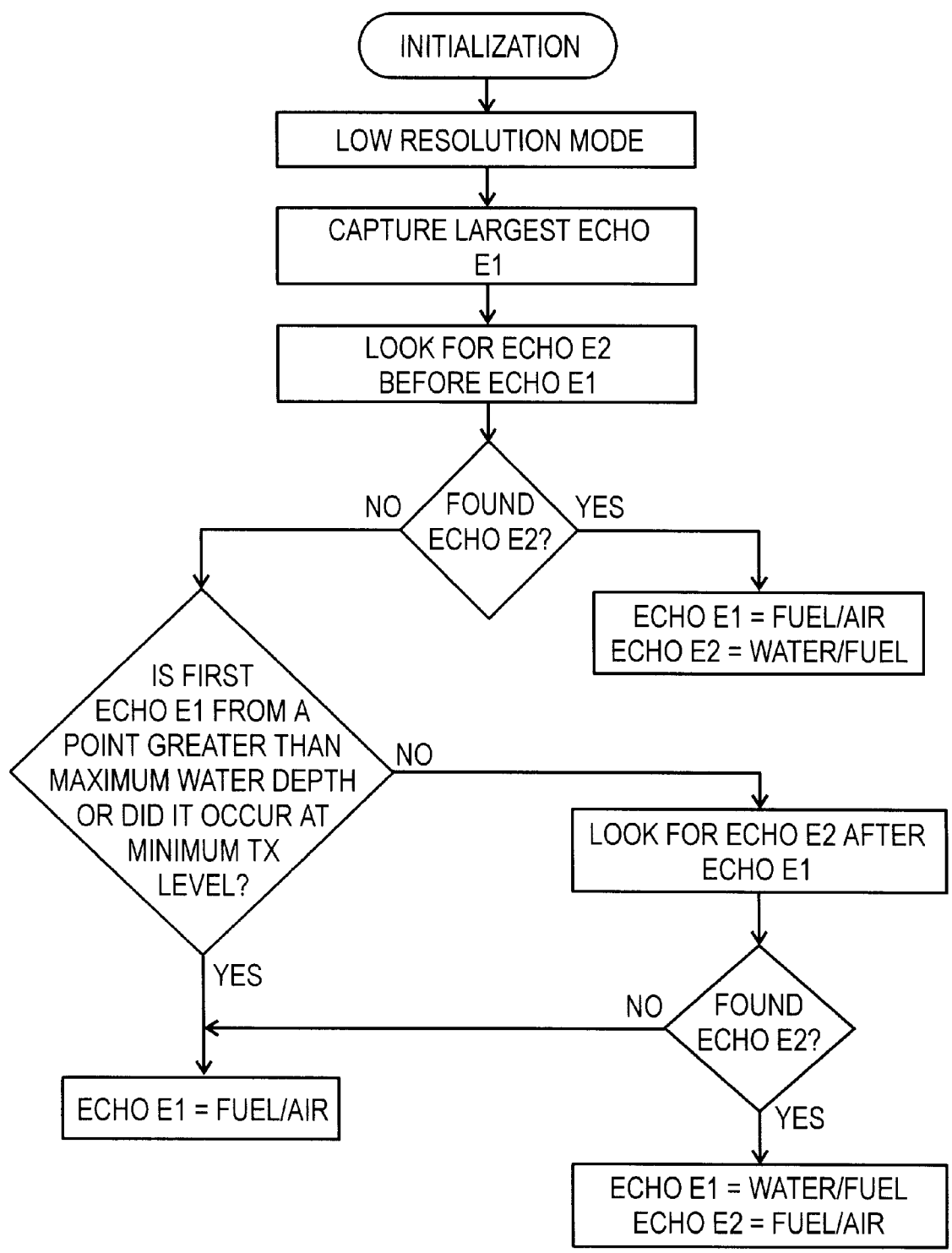
FIG. 5 illustrates in flow chart form the operation of the system in the profiling mode.

When the system is initially powered up, the system will operate in a first mode of operation which is referred to as the low resolution mode. This initial operation is shown in a flow diagram as FIG. 5. In the low resolution mode, the system will operate to adjust the transmit signal level of pulse generator 260 and the receive signal gain of receive amplifier 270 to capture the largest echo E1. The time at which the echo is received is noted as are both the transmit signal level and the receive gain. Next, the system will look for another echo E2 prior to the largest echo E1. If echo E2 is detected the echo E2 is from the fuel/water interface and echo E1 is from the fuel/air interface. If echo E2 is not detected, then two determinations are made. First, it is determined whether the depth represented by the time of the echo E1 represents a depth which is greater than the maximum water depth. In this instance, then echo E1 is from the fuel/air interface. Alternatively, if echo E1 is received as a result of utilizing the minimum sensitivity level, then echo E1 is from the fuel/air interface.

If the depth is not greater than the maximum water depth and the minimum sensitivity level was not utilized then the echo validation time, i.e., the time window during which an echo may be captured (as described in the preceding paragraph), is increased and the system attempts to identify an echo E2 after echo E1. If an echo E2 is detected, then echo E2 is from the fuel/air interface and the echo E1 is reflected from the fuel/water interface. If echo E2 is not detected, then the echo E1 is from the fuel/air interface. At this time, the system will attempt to operate in a high resolution mode.

The system may not be able to switch to the high resolution mode if, for example, the surface of the fuel/air interface is moving during high resolution initialization as it would if the tank is being filled.

Initially, when operating in the high resolution mode, the signal level of pulse generator 260 determined in the low resolution mode is utilized as well as the echo validation time window determined in the low resolution mode for the fuel/air interface and the fuel/water interface. The waveform for the fuel/air interface is now profiled to choose a specific echo ring to trigger on for the fuel/air echo.

The submerged reflectors are then profiled. To profile the reflector echoes the threshold of the receiver is set to a minimum value and a signal is transmitted from the transducer. The times of all echoes received which are less than the time for the fuel/air interface to be received are stored. These times will be the echo times for each submerged reflector. The system will then profile each of the reflector echo waveforms. If at least two reflectors are identified, then the system will operate in the high resolution mode.

As a result of profiling, the pulse generator signal levels are set, the receive thresholds for each reflector are set and the time windows are determined for the fuel/air interface. One hundred measurements are then taken for the fuel/air depth and the average for these measurements is taken to determine the echo time from the surface. Similarly, one hundred measurements are taken for each submerged reflector and water/fuel interface and averaged for each. The averaged numbers at this time are high resolution numbers for each reflector and for the fuel/air interface.

Figure 6:
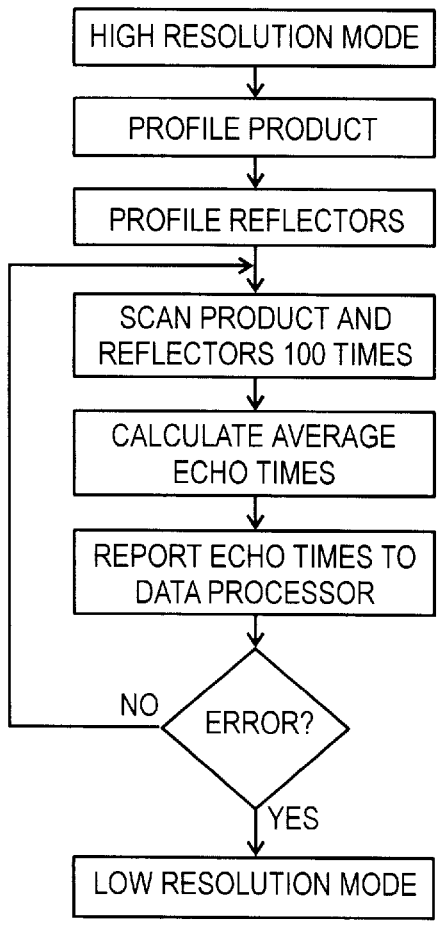
FIG. 6 illustrates in flow chart form one aspect of system operation.

The high resolution mode is shown in the flow diagram of FIG. 6. The high resolution mode is repeated periodically without going back into the low resolution mode. No reprofiling occurs during these cycles. In each cycle of the high resolution mode the depth of the product in the tank is determined by determining the time difference between the fuel/air interface and the top submerged reflector and multiplying that time difference by the sonic velocity between the top two submerged reflectors and adding the height of the top submerged reflector. In the event that an error is detected in any of the operations, such as might occur when the tank is being filled, the system will switch to operate in the low resolution mode. In the low resolution mode, the echo time from the fuel/air interface is determined and is multiplied by product sound velocity which is determined from a value determined from the last high resolution mode measurements. This value of product sound velocity is calculated from the product depth which was determined as described above for the high resolution mode and dividing that depth by the echo time for the fuel/air reflection.

Figure 7:
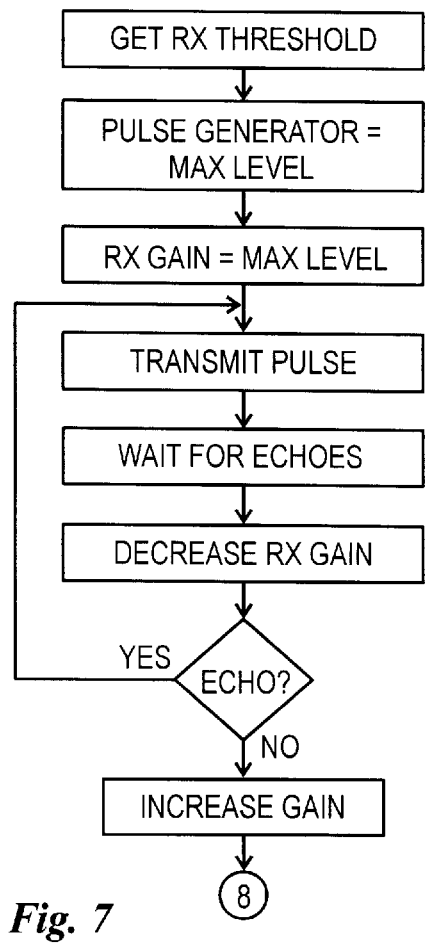
FIG. 7 illustrates in flow chart form a second aspect of the system.
Figure 8:
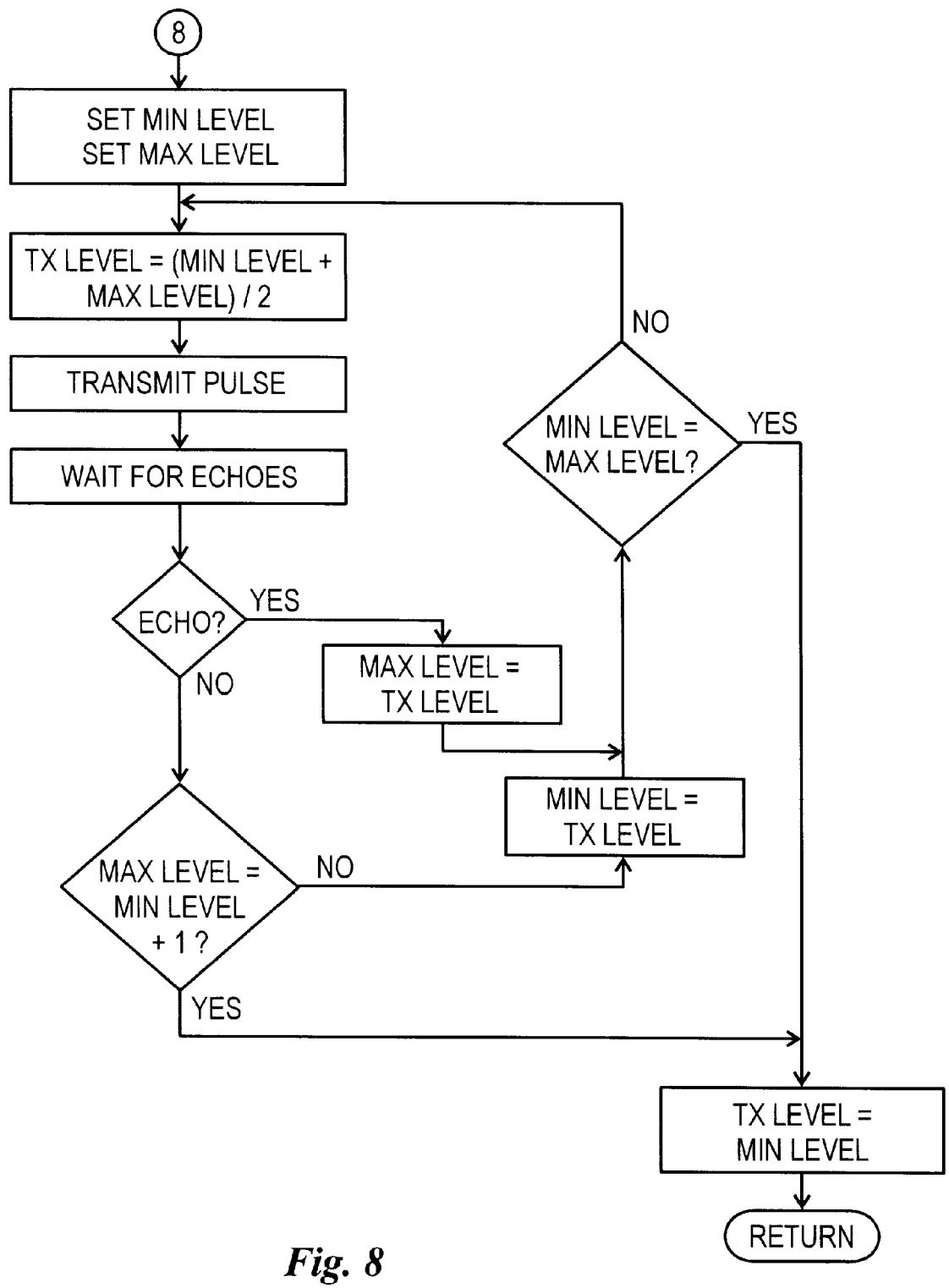
FIG. 8 illustrates in flow chart form a third aspect of system operation.

To profile the echo waveform the procedure set forth in FIGS. 7 and 8 is initially followed.

Initially, the receive threshold of comparator 275 is set to 1.5 volts via D/A convertor 276. The gain of amplifier 270 is set to its maximum value and the signal level of pulse generator 260 is set to its maximum level.

The pulse generator 260 is triggered and transducer 320 generates an ultrasonic signal. After an echo is received, using amplifier 270, the receive gain of amplifier 270 is decreased and is decreased after each pulse until no echo is received. After no echo is received the gain of amplifier 270 is increased by one step.

The pulse generator level is then set by a successive approximation technique as set forth in FIG. 8.

Figure 4:
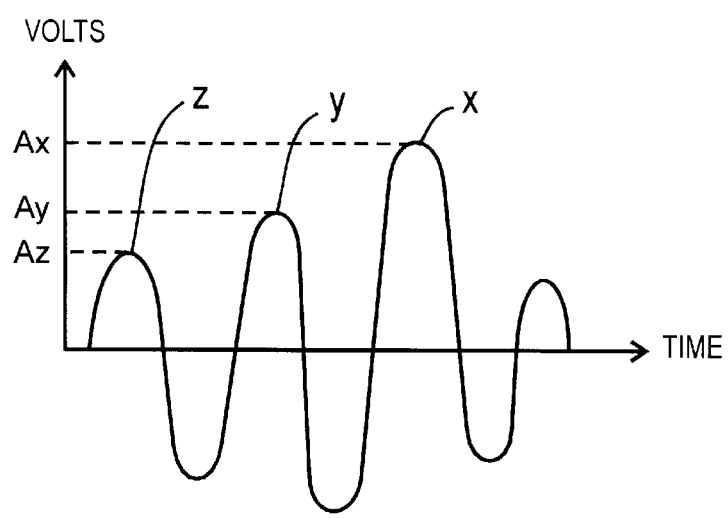
FIG. 4 illustrates a signal waveform.

This system provides an improved method for triggering on ultrasonic echoes. On an initial echo scan, each echo is profiled. The profiled echoes include calibration reflector and gasoline surface echoes. For each profiled echo, the amplitudes Ax, Ay, Az of each ring x, y, z in FIG. 4 are measured, the amplitude differences between the measured amplitudes are computed, and the trigger sensitivity is selected for the largest computed amplitude difference, e.g., /Ax−Ay/, and that position of the waveform will be utilized for triggering for that particular echo. On subsequent echo scans, the selected trigger sensitivities are used to trigger on each selected echo rings, and the echo scanning is quick because the echoes are not profiled again. As a result, the echo times for each echo are reliable and consistent until another echo scan initialization is required.

In the present invention, the method for determining the liquid depth uses the speed of sound between the last two submerged reflectors 370 for measuring the depth. With reference to FIG. 3, the known depths for the reflectors 370 are designated as Xa through Xg, with Xa being the lower reflector. The measured echo times for the reflectors 370 are designated as ta through tg. The calculated depth and measured echo time for the gasoline are designated as Xz and tz. The ultrasonic system measures tf, tg, and tz. Then Xz is calculated with Xz=(Xg−Xf)/(tg−tf)*(tz−tg)+Xg.

In one previous method determines the liquid depth by using the average speed of sound Vavg between the transducer and the last submerged reflector. However, Vavg does not accurately represent the speed of sound between the submerged reflector and the gasoline surface. Speed of sound changes in the gasoline at lower depths affect Vavg resulting in gasoline depth errors.

The method for determining the gasoline temperature is improved by weighting the temperature in each submerged calibration reflector zone by the gasoline volume in the zone. The measured temperature at the transducer is designated as Tt. Assume in this case, four calibration reflectors are submerged, but at other times the number of submerged calibration reflectors varies. The known depths for the calibration reflectors are designated as Xa, Xb, Xc, and Xd. The measured echo times for the calibration reflectors are designated as ta, tb, tc, and td. The calculated speed of sound between the transducer and the first calibration reflector, the first and second calibration reflector, the second and third calibration reflector, and third and fourth calibration reflector are designated as vta, vab, vbc, and vcd. The speeds of sound are calculated with v12=(X2−X1) /(t2−t1)/2). Once the speeds of sound are calculated, they are saved as initial speeds of sound designated as vtai, vabi, vbci, and vcdi. Along with the initial speeds of sound, the transducer temperature is saved as the initial temperature designated as Tti. On subsequent readings, current speeds of sound are calculated. The calculated temperature changes are designated as ΔTta, ΔTab, ΔTbc, and ΔTcd. The temperature changes are calculated with ΔT12=(v12−v12i)/(Δv/ΔT) where Δv/ΔT is a predetermined constant. The current temperatures are calculated with T12 =ΔT12+Tti. The calculated temperatures are designated as Tta, Tab, Tbc, and Tcd. The gasoline volumes in each calibration reflector zone are designated as Vta, Vab, Vbc, and Vcd. The volume weighted temperature, Tvw, is calculated with Tvw= (Tta*Vta+Tab*Vab+Tbc*Vbc+Tcd*Vcd)/ (Vta+Vab+Vbc+Vcd).

A previous method determines the temperature by using the average speed of sound Vavg between the transducer and the last submerged reflector. However, Vavg does not accurately represent the speed sound of the gasoline volume because the volume is not equally distributed along the temperature measuring axis. Speed of sound changes in tank areas of smaller volume are weighted too heavily as compared to tank areas of larger volume resulting in gasoline temperature change errors. Thus, my method obtains a higher accuracy in determining the temperature.

It will be apparent to those skilled in the art that many variations may be made to the illustrative embodiment of the invention described without departing from the spirit or scope of the invention. The invention is to be limited only by the scope of the claims appended hereto.

What is claimed is:

1. A method of profiling a waveform of echo signals received by a transducer in an ultrasonic fluid measuring system, said method comprising:

measuring the amplitudes of peaks of cycles of said waveform;

calculating the absolute values of differences of said amplitudes between adjacent cycles of said waveform;

identifying the cycle of said waveform having the largest absolute value difference over an adjacent cycle; and utilizing said identified cycle of said waveform to detect subsequent ones of said echo signals.

* * * * *